United States Patent [19]

Ogle, II

[11] Patent Number: 4,869,384

[45] Date of Patent: Sep. 26, 1989

[54] PACKAGE FOR TOXIC AND DANGEROUS DRUGS

[75] Inventor: George B. Ogle, II, Alta Loma, Calif.

[73] Assignee: International Medication Systems Limited, South El Monte, Calif.

[21] Appl. No.: 142,965

[22] Filed: Jan. 12, 1988

[51] Int. Cl.$^4$ .................................... A61M 5/00

[52] U.S. Cl. .................................... 215/247; 604/414

[58] Field of Search .................... 215/247, 248, 249; 604/414, 411, 905, 192

[56] References Cited

U.S. PATENT DOCUMENTS

| | | | |
|---|---|---|---|
| 2,908,274 | 10/1959 | Bujan | 215/247 X |
| 4,232,669 | 11/1980 | Nitshke | 604/192 |
| 4,516,967 | 5/1985 | Kopfer | 604/87 |
| 4,552,277 | 11/1985 | Richardson et al. | 215/247 X |

*Primary Examiner*—Donald F. Norton
*Attorney, Agent, or Firm*—Christie, Parker & Hale

[57] ABSTRACT

A medicament package comprising a rigid container having an end wall, side walls and an open end.

A resilient closure which seals said open end of said rigid container, said resilient closure having an upper and lower portion, the lower portion being received in the open end of said rigid container and sealing same, the upper portion of said resilient closure projecting beyond the outer extremity of the open end of said container.

A fluid pathway extending longitudinally through both portions of said resilient closure, said fluid pathway being bridged by an imperforate diaphragm within said upper portion of said resilient closure.

5 Claims, 2 Drawing Sheets

PACKAGE FOR TOXIC AND DANGEROUS DRUGS

BACKGROUND OF THE INVENTION

A significant number of drugs are toxic, mutagenic or otherwise dangerous if allowed to contact, or to be inhaled or ingested, in an uncontrolled or improper manner, into a human being. Health care professionals, including physicians, nurses, and others, are particularly subject to exposure to these hazards.

The anti-tumor drugs are an example of a class of drugs presenting these hazards.

At present, these drugs are usually marketed in glass vials or ampules in either powder or liquid form. If in powder form, the drug must be reconstituted by the addition of diluent just prior to administration. In all cases, the drug in the liquid state must be transferred to a hypodermic syringe or similar device for subsequent direct injection into the patient, or for addition to an intravenous solution bottle or bag to permit infusion of the drug to the patient.

The present invention concerns a novel container for hazardous drugs, and means for transferring such drugs to a syringe in a safer manner. The present invention significantly reduces the risk of inadvertent finger and hand punctures stemming from inadvertent contact with the scarf of the syringe needle. In another important aspect, this invention reduces the likelihood of accidental leakage and spillage of the drug onto the hands and fingers, and adjacent work surfaces. It is sincerely believed that this invention presents a significant advance in the packaging and handling of hazardous drugs.

SUMMARY OF THE INVENTION

Briefly, this invention comprises a package for toxic or hazardous medicament. The package includes a container having an end wall, side walls, and an open end;

a resilient closure which seals said open end of said rigid container, said resilient closure having an upper and lower portion, the lower portion being received in the open end of said rigid container and sealing same, the upper portion of said resilient closure projecting beyond the outer extremity of the open end of said container; and a fluid pathway extending longitudinally through both portions of said resilient closure, said fluid pathway being bridged by an imperforate diaphragm within said upper portion of said resilient closure.

This invention also includes a toxic or hazardous medicament package comprising a rigid container having an end wall, side walls and an open end; a resilient closure which seals said open end of said rigid container, said resilient closure having an upper and lower portion, the lower portion being received in the open end of said rigid container and sealing same, the upper portion of said resilient closure projecting beyond the outer extremity of the open end of said container; a fluid pathway extending longitudinally through both portions of said resilient closure, said fluid pathway being bridged by an imperforate diaphragm within said upper portion of said resilient closure and a syringe, a cannula terminating at a scarf, a protective sheath surrounding said cannula and extending beyond said scarf, said sheath snugly receiving said upper portion of said resilient closure, said cannula being adapted to pierce said diaphram, whereby the contents of said rigid container can be transferred to said syringe without leakage of said toxic or hazardous medication.

It is an object of my invention to provide a novel medicament package.

It is an object of this invention to reduce the hazard to medical personnel presented by certain anti-tumor and other toxic drugs.

Still further, it is an object of this invention to provide a new means of transferring dangerous and toxic drugs to a hypodermic syringe.

These and other objects and advantages of this invention will be apparent from the more detailed description which follows taken with the accompanying drawings.

DESCRIPTION OF THE PREFERRED EMBODIMENTS

Turning to the drawings.

Figure 1:
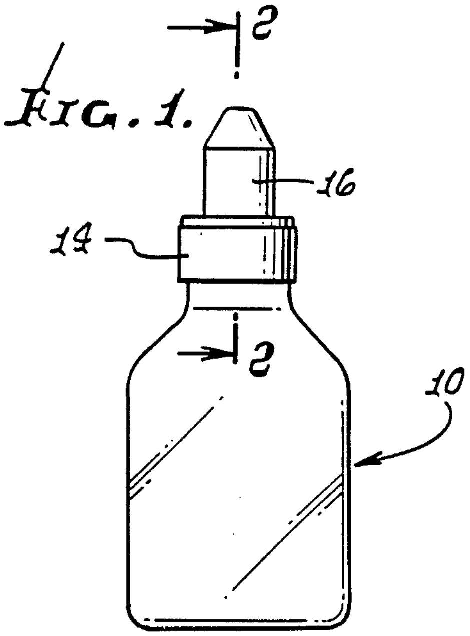
FIG. 1 is a side view of a preferred embodiment of the novel toxic medicament package of this invention.
Figure 2:
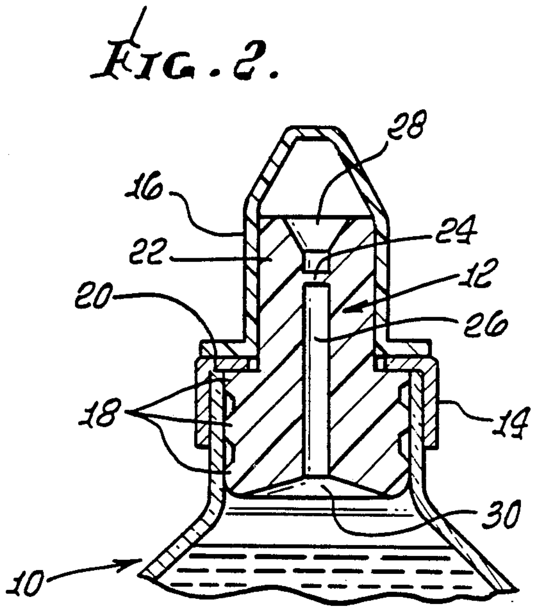
FIG. 2 is a sectional view taken along the line 2—2 in FIG. 1.

Considering the drawings in more detail, FIGS. 1 and 2 show the novel medicament package where 10 is the rigid bottle containing the toxic medication, 12 is the stopper, 14 is the crimped metal retainer collar which extends around the bottle 10 and aids in holding stopper 12 in place and 16 is the protective cover.

The stopper 12 is normally a resilient material such as rubber and has a plurality of sealing rings 18 on its lower portion which are received in the open end 20 of the bottle 10. The upper portion 22 of stopper 12 projects beyond the outer extremity of the open end 20 of bottle 10 and generally is smaller in diameter than said lower portion. The transition between the upper and lower portions is an offset which abuts collar 14. The stopper 12 is provided, preferably within said upper portion 22, with an imperforate diaphragm 24, which bridges the axial, centrally disposed, and longitudinally extending fluid pathway 26. As shown in FIG. 2, the length of the upper portion of the stopper projecting beyond the outer extremity of the open end of the bottle is at least several times greater than the longitudinal thickness of the diaphragm. In addition, the longitudinal thickness of the diaphragm is less than the transverse dimension of the fluid pathway. The upper and lower portions of stopper 12 are concentric with each other and have concave end surfaces 28 and 30, respectively, the centers of which are concentric with said fluid pathway.

The protective cover 16 is held on the outer portion 22 of stopper 12 by a slight interference fit so that the cap will not fall off, but still can be readily removed by hand.

The bottle 10 can be replaced by a cylindrical shell vial, ampule or the like.

Figure 3:
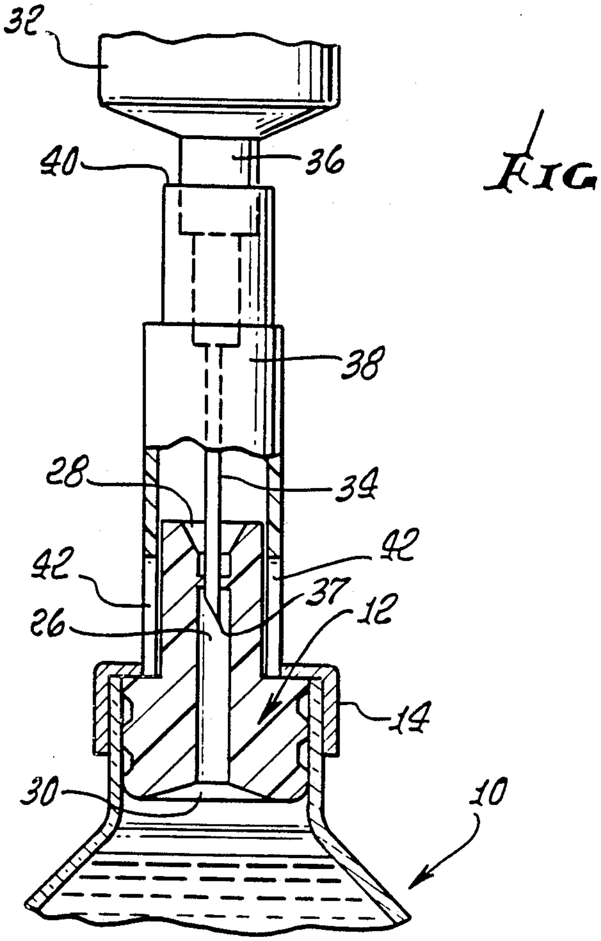
FIG. 3 is a side and partial sectional view showing the transfer of toxic drug from the package to the preferred form of syringe used in the practice of my invention.
Figure 4:
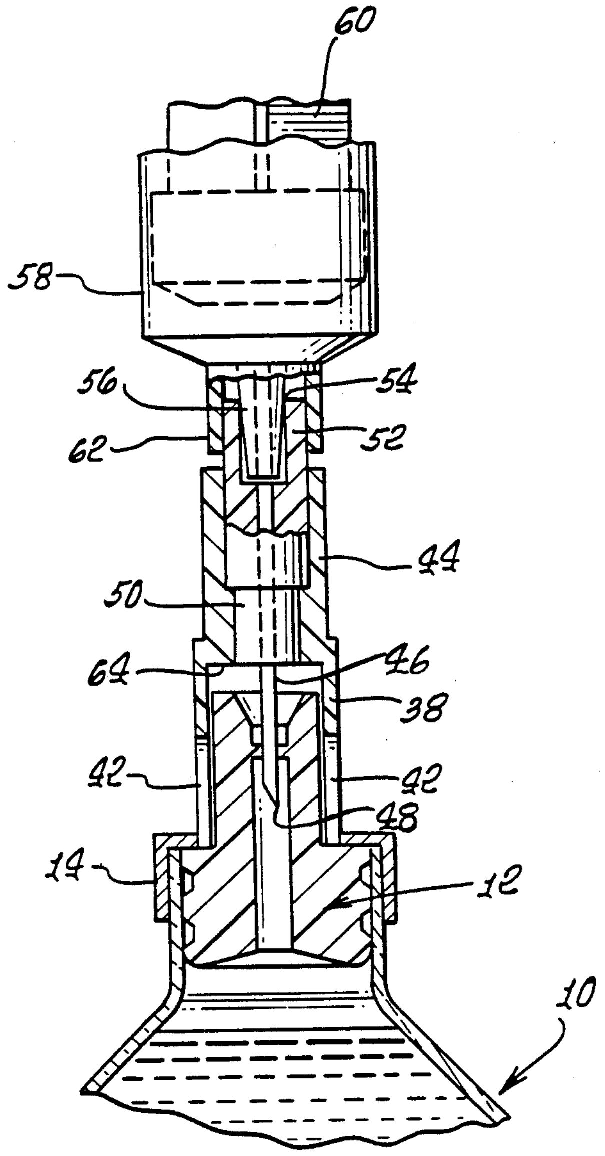
FIG. 4 shows, in sectional view, another embodiment of the present invention.

The embodiments of FIGS. 3 and 4 include structure which is disclosed in applicant's copending U.S. patent application Ser. No. 74,721, filed July 21, 1987, now U.S. Pat. No. 4,834,716, issued May 30, 1989, the disclosure of which is expressly incorporated herein by reference at this point.

As shown in FIG. 3, a protective device is present which is a generally cylindrical sheath 38 forming a closed end 40 by seal or integral formation with boss 36 of the syringe 32. If the sheath is not integral with the syringe, it can be removable by a slip interference fit on the boss.

The sheath 38 terminates in an open end which is disposed beyond the end of scarf 37 of cannula 34.

The sheath 38 preferably has two diametrically disposed cutouts 42. One cutout is actually sufficient, but two cutouts provide greater convenience to the users. The dimensions of cutouts 42 are such as to accommodate the tubular Y-site portion (not shown) of a typical I.V. or "giving set" which is quite familiar to those skilled in the art.

The contents of the syringe can be injected into the patient via the Y-site in the usual way, with the important difference being that the health care provider is not apt to suffer an accidental needle puncture in the process of manually manipulating the syringe and Y-site to make the necessary connection to hook-up.

Prior to use, the sheath 38 can be provided with a removable cap or cover (not shown) forming an aseptic seal with said sheath 38.

In FIG. 4 the sheath 44 is a separate piece having cutouts 42 (previously explained), cannula 46, scarf 48 and boss 50 to which cannula 46 is affixed or secured. The boss 50 has a cylindrical projection 52 with an open end 54. The open end 54 is adapted to sealably receive the Luer fitment 56 of syringe 58 (having a reciprocatable plunger 60). The projection 52 also has slidably received around it in a snug fit the Luer skirt 62. The syringe 58 may also have the structure shown in U.S. Pat. No. 3,376,866, the disclosure of which is incorporated herein by reference.

In this way, the toxic or hazardous contents of bottle 10 can be transferred to syringe 58, without risk of spillage, by inversion of the entire assembly shown in FIG. 4, followed by withdrawal of plunger 60, which action draws the contents of the bottle 12 into the syringe. If any fluid leaks out of pierced stopper 12, it is caught in the bottom 64 of sheath 38.

The present invention affords several significant safeguards. First, the interaction of the stopper with the sheath provides alignment and precise needle puncture so that leakage of toxic material is avoided. Without the alignment structures of this invention, the repeated punctures necessary for typical multiple-dose vials results in not one, but several holes in the diaphragm, causing leakages and spills. This cannot happen in the present invention where the scarf of the cannula is aligned by the sheath with the stopper, and the same hole in the diaphragm is repeatedly and consistently struck.

Secondly, in filling the syringe, the container 10 is always inverted and above the syringe, which has the cannula pointed up. Even if a small leakage occurred around the cannula via the hole created by the cannula piercing the diaphragm, these drops would be caught inside the sheath 38 and could not spill on the hands and fingers.

Thirdly, the diametrically disposed cutouts on the sheath permit safe injection of the toxic contents of the syringe at the "Y" site of an IV set, as is explained in my above-mentioned U.S. Pat. No. 4,834,716.

In addition, generally hospitals now instruct nurses, etc. not to recap needles but rather to discard them into special containers. Most of accidental needle punctures come from the used needles when personnel are trying to recap them. In the present invention, because the needle is recessed, there is no need to use the above precautions.

Thus, it is apparent that my invention provides significant safety advantages.

Having fully described the invention, it is intended that it be limited solely by the lawful scope of the appended claims.

I claim:

1. A toxic or hazardous medicament package comprising a rigid container having an end wall, side walls, and an open end; a resilient closure which seals said open end of said rigid container, said resilient closure having an upper end lower portion, the lower portion being received in the open end of said rigid container and sealing same, the upper portion of said resilient closure projecting beyond the outer extremity of the open end of said container; a fluid pathway extending longitudinally through both portions of said resilient closure, said fluid pathway being bridged by an imperforate diaphragm within said upper portion of said resilient closure; and a cap enclosing and sealing the upper portion of the resilient closure.

2. A toxic or hazardous medicament package comprising a rigid container having an end wall, side walls and an open end; a resilient closure which seals said open end of said rigid container, said resilient closure having an upper and lower portion, the lower portion being received in the open end of said rigid container and sealing same, the upper portion of said resilient closure projecting beyond the outer extremity of the open end of said container; a fluid pathway extending longitudinally through both portions of said resilient closure, said fluid pathway being bridged by an imperforate diaphragm within said upper portion of said resilient closure and a syringe with a cannula terminating at a scarf, a protective sheath surrounding said cannula and extending beyond said scarf, said sheath snuggly receiving said upper portion of said resilient closure, said cannula being adapted to pierce said diaphram, whereby the contents of said rigid container can be transferred to said syringe without leakage of said toxic or hazardous medication.

3. The package of claim 2 wherein said cannula is affixed to and carried by carrying means affixed to said sheath.

4. A toxic or hazardous medicament package comprising a container having an open end; a resilient closure which seals said open end of the rigid container, the resilient closure having an upper and lower portion, the lower portion being received in the open end of the rigid container and sealing same, the upper portion of the resilient closure projecting beyond the outer extremity of the open end of said container; a fluid pathway extending longitudinally through both portions of said resilient closure, said fluid pathway being bridged by an imperforate diaphragm within said upper portion of said resilient closure; the length of the upper portion of the resilient closure projecting beyond the outer extremity of the container being at least several times greater than the longitudinal thickness of the diaphragm.

5. The package according to claim 4 in which the longitudinal thickness of the diaphragm is less than the transverse dimension of the fluid pathway.

* * * * *